Figure 1:
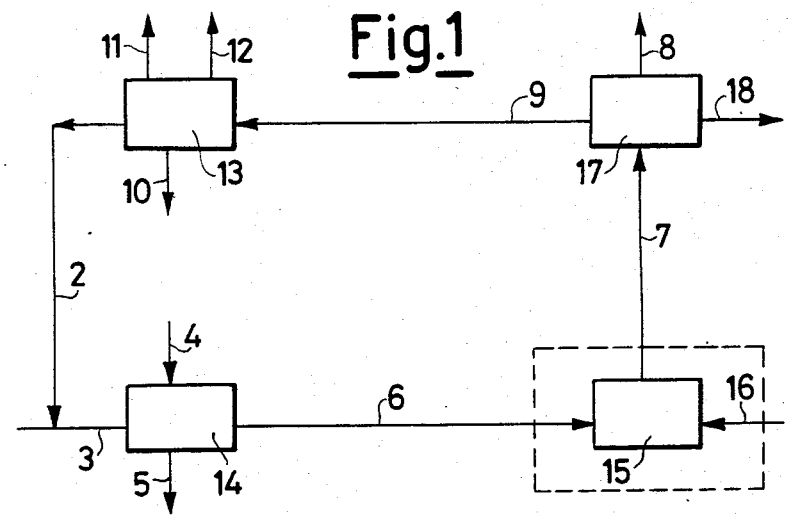

United States Patent [19]

Sandrin

[11] Patent Number: 4,513,153

[45] Date of Patent: Apr. 23, 1985

[54] INTEGRATED PROCESS FOR PRODUCING TERT.BUTYL ALKYL ETHERS AND BUTENE-1

[75] Inventor: Romedio Sandrin, Milan, Italy

[73] Assignee: Snamprogetti S.p.A., Milan, Italy

[21] Appl. No.: 491,067

[22] Filed: May 3, 1983

[30] Foreign Application Priority Data

May 20, 1982 [IT] Italy ................................ 21383 A/82

[51] Int. Cl.$^3$ .............................................. C07C 41/06
[52] U.S. Cl. ...................................... 568/697; 203/43; 203/44; 203/45; 203/46; 203/57; 585/315; 585/332
[58] Field of Search ................... 568/697; 203/43–46, 203/57; 585/315, 332

[56] References Cited

U.S. PATENT DOCUMENTS 4,287,379  9/1981  Brunner et al. .................... 568/697
4,320,232  3/1982  Volkamer et al. .................. 568/697

FOREIGN PATENT DOCUMENTS 55361  7/1982  European Pat. Off. .

OTHER PUBLICATIONS

Muddarris et al., Hydrocarbon Processing, Oct. 1980, 91–95.
Scheeline et al., Process Economic Reviews, Dec. 1978, pp. 1–4, 7–17, FIG. 3.1.
Choudhary, Chemical Industry Developments, 1974, pp. 32–41.

*Primary Examiner*—Howard T. Mars
*Attorney, Agent, or Firm*—Hedman, Gibson, Costigan & Hoare

[57] ABSTRACT

Tert.butyl alkyl ethers are produced from a $C_4$ hydrocarbon feedstock containing isobutene, and the butene-1 is recovered at high purity by extractive distillation of the isobutene-free $C_4$ hydrocarbon stream in the presence of a solvent chosen from acetone, acetonitrile, dimethylformamide, methanol, n-methylpyrrolidone, formylmorpholine and furfural.

After removing the solvent, the extract is rectified, and the butene-1 separates as overhead product of high purity.

5 Claims, 2 Drawing Figures

INTEGRATED PROCESS FOR PRODUCING TERT.BUTYL ALKYL ETHERS AND BUTENE-1

This invention relates to an integrated process for producing tert.butyl alkyl ethers and butene-1.

More specifically, the present invention relates to an integrated process for producing tert.butyl methyl ether (MTBE) and butene-1. Many processes are known in the art for producing tert.butyl alkyl ethers, consisting of reacting isobutene, possibly contained in hydrocarbon streams of various origin and in particular in the stream originating from steam cracking or catalytic cracking plants, with an alcohol, preferably methanol or ethanol, in the presence of an acid ion exchange resin.

In this respect, reference can be made to Italian Pat. Nos. 1,012,686, 1,012,687 and 1,012,690.

The known processes allow an almost total isobutene conversion, but in the case of $C_4$ hydrocarbon feedstocks, the other components remain practically unchanged, and cannot therefore be immediately utilised as a petrol component.

The process according to the present invention allows the conversion of part of the components of the hydrocarbon feedstock with 4 carbon atoms, other than isobutylene, into tert.butyl alkyl ethers, together with the isobutene originally contained in said feedstock, and at the same time also leads to the production of pure butene-1. The process according to the present invention consists of the following stages:

(1) Separating the butadiene from the $C_4$ hydrocarbon feedstock to a residual content of less than 0.5% by weight.

(2) Feeding the $C_4$ hydrocarbon feedstock, either free or substantially free of butadiene, to a tert.butyl alkyl ether synthesis section, said synthesis section being filled with catalyst constitituted by an acid ion exchange resin, preferably of the sulphonated divinylbenzene-styrene type.

(3) Reacting the isobutene contained in the $C_4$ hydrocarbon feedstock of point (2) with an aliphatic alcohol fed to said synthesis section, the molar ratio of the alcohol to the isobutene being between 0.9 and 1.3, the reaction product being a tert.butyl alkyl ether.

(4) Separating the tert.butyl alkyl ether from the $C_4$ hydrocarbons by distillation either in the same reaction zone or in a separate zone.

(5) Extractive distillation of the $C_4$ hydrocarbon feedstock residue in the presence of a solvent chosen from acetone, acetonitrile, dimethylformamide, methanol, n-methylpyrrolidine, formylmorpholine and furfural, separating as overhead product most of the $C_4$ saturated hydrocarbons and the lighter hydrocarbons ($C_3$), and as bottom product the extract constituted by butene-1, butene-2, the remainder of the $C_4$ saturated hydrocarbons and the heavier hydrocarbons ($C_5+$).

(6) Stripping the extract in order to separate the solvent from the remainder of the feedstock, the solvent then being recycled to the extractive distillation.

(7) Distilling the remainder of the feedstock of point (6), separating as overhead product pure butene-1 and as bottom product all the other components and part of the butene-1.

(8) Feeding the bottom fraction of point (7) to an isomerisation stage where the butene-2 and unrecovered butene-1 are converted partly into isobutene, to obtain a hydrocarbon fraction containing essentially butene-1, butene-2 and isobutene in which the butene-1/butene-2 molar ratio corresponds practically to thermodynamic equilibrium, whereas the isobutene/linear butene molar ratio lies between 0.3 and 0.6.

(9) Separating the hydrocarbon fraction containing butene-1, butene-2 and isobutene of point (8) from the heavy products.

(10) Feeding the isomerised fraction containing butene-1, butene-2 and isobutene and possibly also part of the heavy products to the tert.butyl alkyl ether synthesis section, either directly or after mixing with the $C_4$ hydrocarbon stream which is free or substantially free of butadiene.

The $C_4$ hydrocarbon feedstock normally also contains $C_3$ and $C_5$ components, and possibly other non-hydrocarbon components.

The $C_4$ feedstock normally comprises $C_3$ hydrocarbons, isobutane, isobutene, butene-1, n-butane, trans butene-2, cis butene-2, and $C_5$ hydrocarbons. The $C_3$ and $C_5$ hydrocarbons are in small quantities, and the others can be in relative quantities which vary greatly according to its origin.

In order to obtain a constant molar ratio between butene-1, butene-2 and isobutene, the isomerisation is carried out using a process such as that described in Italian Pat. No. 1,017,878, using a catalyst based on silicised alumina such as that described in U.S. Pat. Nos. 4,013,589 and 4,013,590.

It is interesting to note that the process according to the present invention allows not only the tert.butyl alkyl ether but also butene-1 at polymerisation purity (>99.5%) to be obtained.

The process according to the present invention on the one hand allows tert.butyl ether to be obtained in a much greater quantity than is obtainable using isobutene alone as the feedstock, and on the other hand allows butene-1 of very high purity to be separated, and suitably utilising at the same time the butene-2 which would otherwise be lost to advantageous use.

One particular embodiment of the invention uses a section for the selective hydrogenation of butadiene and the acetylenic compounds contained in the feedstock fed to the extractive distillation.

Figure 2:
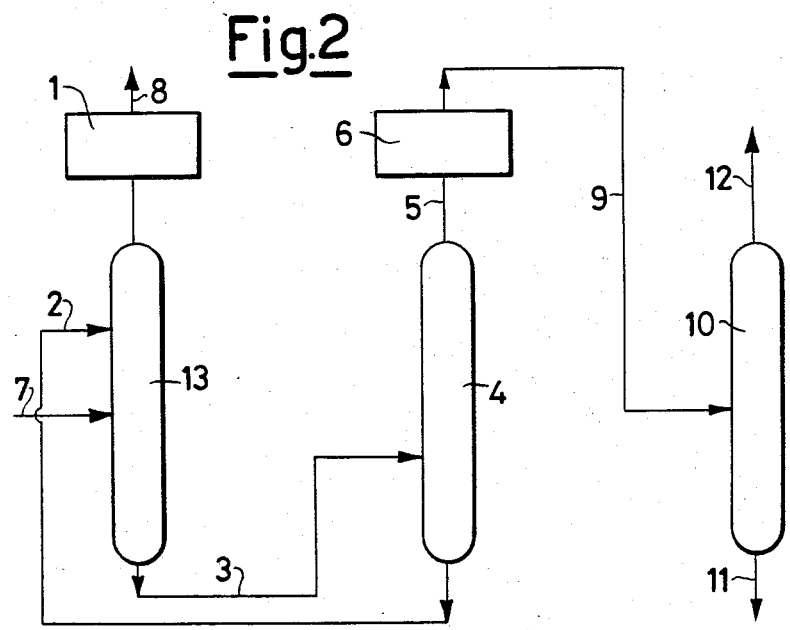

The process according to the present invention will be more apparent from the accompanying FIGS. 1 and 2, which show a non-limiting embodiment of the invention.

FIG. 1 shows the complete cycle in block form, and FIG. 2 shows the butene-1 separation system.

In FIG. 1, (1) indicates the $C_4$ hydrocarbon feedstock free or substantially free of butadiene (2) the stream from the isomerisation unit (13), (3) the inlet feed to the tert.butyl alkyl ether synthesis unit (14), (4) the alcohol feed, in particular methanol, (5) the discharge stream of tert.butyl alkyl ether, $C_5$ hydrocarbons and heavier substances, (6) the feed to the possible unit (15) for the selective hydrogenation of butadiene and the acetylenic compounds, (16) the hydrogen feed, (7) the feed to the extractive distillation unit (17), (18) the separated stream of butene-1, (8) the separated stream of saturated $C_4$ compounds, (9) the feed to the isomerisation unit (13), (11) the heavy hydrocarbon fraction separated from the isomerised stream, (12) a stream of light substantially $C_3$ hydrocarbons, and finally (10) the heavy compounds obtained in the isomerisation. In FIG. 2, the feed (7) to the extractive distillation (13) is fed to the centre or in proximity to the centre of the column, while the extractive solvent (2) is fed in proximity to the top of the column (13).

A stream (8) formed substantially of saturated $C_4$ hydrocarbons and lighter products is obtained from the extractive distillation column (13).

A system (1) is provided for removing solvent traces entrained in the overhead stream, consisting of a water wash possibly followed by the stripping of the water.

The bottom product (3) of the column (13) is fed to the stripper (4) to obtain as bottom product the solvent (2) which is recycled, and as overhead product a stream (5) consisting of butene-1, butene-2 and heavy hydrocarbons. The stream (5) is freed of the entrained solvent at (6) by a process similar to that provided for the stream (8), and the purified stream (9) is fed to the distillation column (10), which as its overhead product provides a stream of butene-1 (12), and as its bottom product, by way of (11), a stream of butene-2 with small quantities of butene-1, n-butane and the heavier compounds. Some examples are given hereinafter in order to better illustrate the invention, but without limiting it in any way.

EXAMPLE 1

Reference is made to the scheme of FIG. 1, and Table 1 shows the composition of the various streams.

The alcohol used was methanol, and the extractive solvent was acetonitrile.

Selective hydrogenation was not used in the test of this example.

TABLE 1

| | 1 | | 2 | | 3 | | 4 | | 5 | | 6 | |
|---|---|---|---|---|---|---|---|---|---|---|---|---|
| | kg/h | % | kg/h | % | Kg/h | % | Kg/h | % | Kg/h | % | Kg/h | % |
| $C_3^-$ | 192 | 0.5 | 456 | 1.6 | 648 | 1 | | | | | 646 | 1.45 |
| isobutane | 504 | 1.3 | 122 | 0.4 | 626 | 1 | | | | | 626 | 1.4 |
| isobutene | 15520 | 41.0 | 6375 | 22.0 | 21898 | 32.7 | | | | | 22 | 0.05 |
| butene-1 | 15374 | 40.6 | 4808 | 16.8 | 20242 | 30.2 | | | | | 20242 | 45.2 |
| n-butane | 1005 | 2.7 | 4628 | 16.0 | 5633 | 8.4 | | | | | 5633 | 12.6 |
| trans butene-2 | 3277 | 8.6 | 6497 | 22.4 | 9774 | 14.6 | | | | | 9774 | 21.8 |
| cis butene-2 | 2016 | 5.3 | 5812 | 20.1 | 7828 | 11.7 | | | | | 7828 | 17.5 |
| $C_5^+$ hydrocarbs | | | 214 | 0.7 | 214 | 0.4 | | | 214 | 0.6 | | |
| methanol | | | | | | | 12338 | 100 | | | | |
| MTBE | | | | | | | | | 34211 | 99.4 | | |
| deposits | | | | | | | | | | | | |
| TOTAL | 37888 | 100 | 28972 | 100 | 66860 | 100 | 12338 | 100 | 34425 | 100 | 44773 | 100 |

| | 18 | | 8 | | 9 | | 10 | | 11 | | 12 | |
|---|---|---|---|---|---|---|---|---|---|---|---|---|
| | Kg/h | % | Kg/h | % | Kg/h | % | Kg/h | % | Kg/h | % | Kg/h | % |
| $C_3^-$ | 3 | 0.02 | 645 | 26.2 | | | | | | | 95 | 38.1 |
| isobutane | 20 | 0.15 | 606 | 24.3 | | | | | | | 1 | 0.4 |
| isobutene | 22 | 0.17 | | | | | | | | | 47 | 18.9 |
| butene-1 | 12876 | 99.5 | 3 | 0.1 | 7363 | 2.51 | | | | | 34 | 13.6 |
| n-butane | 21 | 0.16 | 1206 | 49.4 | 4406 | 15.0 | | | | | 22 | 8.9 |
| trans butene-2 | | | | | 9774 | 33.3 | | | | | 28 | 11.2 |
| cis butene-2 | | | | | 7828 | 26.6 | | | | | 22 | 8.9 |
| $C_5^+$ hydrocarbs | | | | | | | | | 92 | 100 | | |
| methanol | | | | | | | | | | | | |
| MTBE | | | | | | | | | | | | |
| deposits | | | | | | | 58 | 100 | | | | |
| TOTAL | 12942 | 100 | 2460 | 100 | 29371 | 100 | 58 | 100 | 92 | 100 | 249 | 100 |

EXAMPLE 2

With reference to FIG. 2, Table 2 gives the data obtained in the extractive distillation by acetonitrile of the hydrocarbon feedstock specified hereinafter (stream 7 of FIG. 2).

TABLE 2

| | 7 | | 2 | | 8 | | 3 | | 9 | | 12 | | 11 | |
|---|---|---|---|---|---|---|---|---|---|---|---|---|---|---|
| | kg/h | % | kg/h | % | kg/h | % | kg/h | % | Kg/h | % | kg/h | % | kg/h | % |
| $C_3^-$ | 648 | 1.45 | | | 645 | 26.2 | 3 | | 3 | 0.01 | 3 | 0.02 | | |
| isobutane | 626 | 1.4 | | | 606 | 24.3 | 20 | 0.02 | 20 | 0.04 | 20 | 0.15 | | |
| isobutene | 22 | 0.05 | | | | | 22 | | 22 | 0.05 | 22 | 0.17 | | |
| butene-1 | 20242 | 45.2 | | | 3 | 0.1 | 20239 | 9.53 | 20239 | 47.8 | 12786 | 99.5 | 7363 | 25.1 |
| n-butane | 5633 | 12.6 | | | 1206 | 49.4 | 4427 | 2.09 | 4427 | 10.5 | 21 | 0.16 | 4406 | 15.0 |
| trans butene-2 | 9774 | 21.8 | | | | | 9774 | 4.6 | 9774 | 23.1 | | | 9774 | 33.3 |
| cis butene-2 | 7828 | 17.5 | | | | | 7828 | 3.7 | 7828 | 18.5 | | | 7828 | 26.6 |
| solvent | | | 170000 | 100 | | | 170000 | 80.06 | | | | | | |
| TOTAL | 44773 | 100 | 170000 | 100 | 2460 | 100 | 212313 | 100 | 42313 | 100 | 12942 | 100 | 29371 | 100 |

I claim:

1. An integrated process for producing tert-butyl alkyl ethers and butene-1 from a $C_4$ hydrocarbon feedstock optionally containing $C_3$ and $C_5$ components and non-hydrocarbon components, the butadiene having been previously separated from said feedstock, comprising (a) feeding the $C_4$ hydrocarbon feedstock which is substantially free of butadiene to a tert-butyl alkyl ether synthesis section which is filled with a catalyst constituted by an acid ion exchange resin, (b) reacting the isobutene contained in the $C_4$ hydrocarbon feedstock with an aliphatic alcohol in order to produce a tert-butyl alkyl ether, (c) separating the tert-butyl alkyl ether from the residual $C_4$ hydrocarbons by distillation, (d) subjecting the residual $C_4$ hydrocarbons to extractive distillation in the presence of a solvent in order to separate most of the C$_4$ saturated hydrocarbons and the lighter hydrocarbons (C$_3$) present as an overhead product from a bottom product which is an extract comprising the solvent, butene-1, butene-2, the remainder of the C$_4$ saturated hydrocarbons and the heavy hydrocarbons (C$_5$+), (e) then subjecting the extract to stripping in order to separate the solvent from the remainder of the extract, (f) recycling the solvent to the extractive distillation, (g) distilling the remainder of the extract to give an overhead fraction constituted by butene-1 and a bottom fraction comprising butene-2 and butene-1 and the balance of the extract, (h) passing the bottom fraction through an isomerization stage in which the butene-2 and the unrecovered butene-1 are partly converted into isobutene to obtain an isomerized hydrocarbon fraction containing butene-1, butene-2 and isobutene, (i) separating said isomerized hydrocarbon fraction from the remainder of the products, and (j) feeding the isomerized hydrocarbon fraction containing butene-1, butene-2 and isobutene to the tert-butyl alkyl ether synthesis.

2. A process according to claim 1, wherein the extractive distillation is carried out in the presence of a solvent selected from the group consisting of acetone, acetonitrile, dimethylformamide, methanol, n-methyl pyrrolidone, formylmorpholine and furfural.

3. A process according to claim 1, in which said acid ion exchange resin in said tert-butyl alkyl synthesis section is of the sulphonated divinylbenzene-styrene type.

4. A process according to claim 1, in which in step (b) the molar ratio of aliphatic alcohol to isobutene is between 0.9 and 1.3.

5. A process according to claim 1, in which the C$_4$ hydrocarbon feedstock in step (a) has a butadiene content of less than 0.5% by weight.

* * * * *